(12) United States Patent
Radulescu et al.

(10) Patent No.: US 11,366,208 B2
(45) Date of Patent: Jun. 21, 2022

(54) SYNCHRONIZED PHASED ARRAY DATA ACQUISITION FROM MULTIPLE ACOUSTIC WINDOWS

(71) Applicant: KONINKLIJKE PHILIPS N.V., Eindhoven (NL)

(72) Inventors: Emil George Radulescu, Ossining, NY (US); Sanghamithra Korukonda, Seattle, WA (US); Jean-luc Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1266 days.

(21) Appl. No.: 15/314,521

(22) PCT Filed: May 27, 2015

(86) PCT No.: PCT/IB2015/053949
§ 371 (c)(1),
(2) Date: Nov. 29, 2016

(87) PCT Pub. No.: WO2015/181731
PCT Pub. Date: Dec. 3, 2015

(65) Prior Publication Data
US 2017/0168148 A1 Jun. 15, 2017

Related U.S. Application Data

(60) Provisional application No. 62/004,968, filed on May 30, 2014.

(51) Int. Cl.
*G01S 7/52* (2006.01)
*A61B 8/00* (2006.01)
(Continued)

(52) U.S. Cl.
CPC ........ *G01S 7/52044* (2013.01); *A61B 8/4477* (2013.01); *A61B 8/461* (2013.01);
(Continued)

(58) Field of Classification Search
None
See application file for complete search history.

(56) References Cited

U.S. PATENT DOCUMENTS 4,468,747 A 8/1984 Leavitt et al.
5,640,959 A 6/1997 Hara et al.
(Continued)

FOREIGN PATENT DOCUMENTS

JP 2010029281 A 2/2010
JP 2015186493 A 10/2015
WO 2014021105 A1 2/2014

*Primary Examiner* — Shahdeep Mohammed

(57) ABSTRACT

In some embodiments, ultrasound receive beamforming yields beamformed samples, based upon which spatially intermediate pixels (232, 242, 244) are dynamically reconstructed. The samples have been correspondingly derived from acquisition through respectively different acoustic windows (218, 220). The reconstructing is further based on temporal weighting of the samples. In some embodiments, the sampling is via synchronized ultrasound phased-array data acquisition from a pair of side-by-side, spaced apart (211) acoustic windows respectively facing opposite sides of a central region (244) to be imaged. In particular, the pair is used interleavingly to dynamically scan jointly in a single lateral direction in imaging the region. The acquisition in the scan is, along a synchronization line (222) extending laterally across the region, monotonically progressive in that direction. Rotational scans respectively from the window pair are synchronizable into a composite scan of a moving object. The synchronization line (222) can be defined by the focuses of the transmits. The progression may strictly increase.

14 Claims, 4 Drawing Sheets

(51) Int. Cl.
*A61B 8/08* (2006.01)
*G01S 15/89* (2006.01)
(52) U.S. Cl.
CPC .......... *A61B 8/483* (2013.01); *G01S 7/52085* (2013.01); *G01S 15/8927* (2013.01); *G01S 15/8993* (2013.01); *A61B 8/0883* (2013.01); *A61B 8/5276* (2013.01)

(56) References Cited

U.S. PATENT DOCUMENTS

| | | | |
|---|---|---|---|
| 2004/0006266 A1 | 1/2004 | Ustuner et al. | |
| 2005/0124887 A1 | 6/2005 | Li | |
| 2008/0294045 A1* | 11/2008 | Ellington | A61B 8/4483 600/447 |
| 2010/0249596 A1* | 9/2010 | Magee | G10K 11/346 600/447 |
| 2011/0178400 A1* | 7/2011 | Specht | A61B 8/4281 600/437 |
| 2012/0095347 A1 | 4/2012 | Adam et al. | |
| 2014/0323872 A1* | 10/2014 | Eom | A61B 8/06 600/459 |

* cited by examiner

SYNCHRONIZED PHASED ARRAY DATA ACQUISITION FROM MULTIPLE ACOUSTIC WINDOWS

This application is the U.S. National Phase application under 35 U.S.C. § 371 of International Application No. PCT/IB2015/053949, filed on May 27, 2015, which claims the benefit of U.S. Provisional Application Ser. No. 62/004,968, filed May 30, 2014. These applications are hereby incorporated by reference herein.

FIELD OF THE INVENTION

The present invention relates to ultrasound scan conversion and, more particularly, to scan conversion of ultrasound acquired from multiple acoustic windows.

BACKGROUND OF THE INVENTION

Once ultrasound phased array data is acquired, a scan conversion is performed to convert the data from polar coordinates to a Cartesian grid. Thus, brightness values can be assigned to pixels of a displayable image. Typically, this transformation of coordinates is performed by weighting each sample as a function of space.

An example of scan conversion is described in U.S. Pat. No. 4,468,747 to Leavitt et al., the entire disclosure of which is incorporated herein by reference.

Leavitt relates to scan conversion from a single acoustic window.

Echocardiography performed with multiple probes or across multiple acoustic windows can provide a larger field of view of the heart. However, this configuration requires registration and synchronization between beams obtained from each view or probe. Several techniques exist to combine the multiple data sets such as ECG gating based acquisition, real time volume registration, etc.

SUMMARY OF THE INVENTION

The above-mentioned techniques of ECG gating based on acquisition and time volume registration are well suited to data acquisition from a single acoustic window.

What is needed is a multi-window acquisition scheme for overcoming motion artefacts, particularly when imaging moving organs such as the heart. Especially during cardiac interventional surgery it is important to image highly mobile objects such as valves in the heart with maximum image quality. One of the key factors for attaining an effective degree of image quality is mitigating motion artefacts. The techniques proposed herein are directed to performing imaging as synchronously as possible. Additionally proposed are methods during scan conversion to mitigate the effect of inevitable cardiac motion.

In an aspect of what is proposed herein, ultrasound receive beamforming yields beamformed samples, based upon which spatially intermediate pixels are dynamically reconstructed. The samples have been correspondingly derived from acquisition through respectively different acoustic windows. The reconstructing is further based on temporal weighting of the samples.

In a related aspect, what is proposed is a method for synchronized ultrasound phased-array data acquisition from a pair of side-by-side, spaced apart acoustic windows respectively facing opposite sides of a central region to be imaged. In particular, the pair is used interleavingly to dynamically scan jointly in a single lateral direction in imaging the region. The acquisition in the scan is, along a synchronization line extending laterally across the region, monotonically progressive in that direction.

Details of the novel, ultrasound acquisition synchronization technology based on multiple acoustic windows are set forth further below, with the aid of the following drawings, which are not drawn to scale.

DETAILED DESCRIPTION OF EMBODIMENTS

Figure 1:
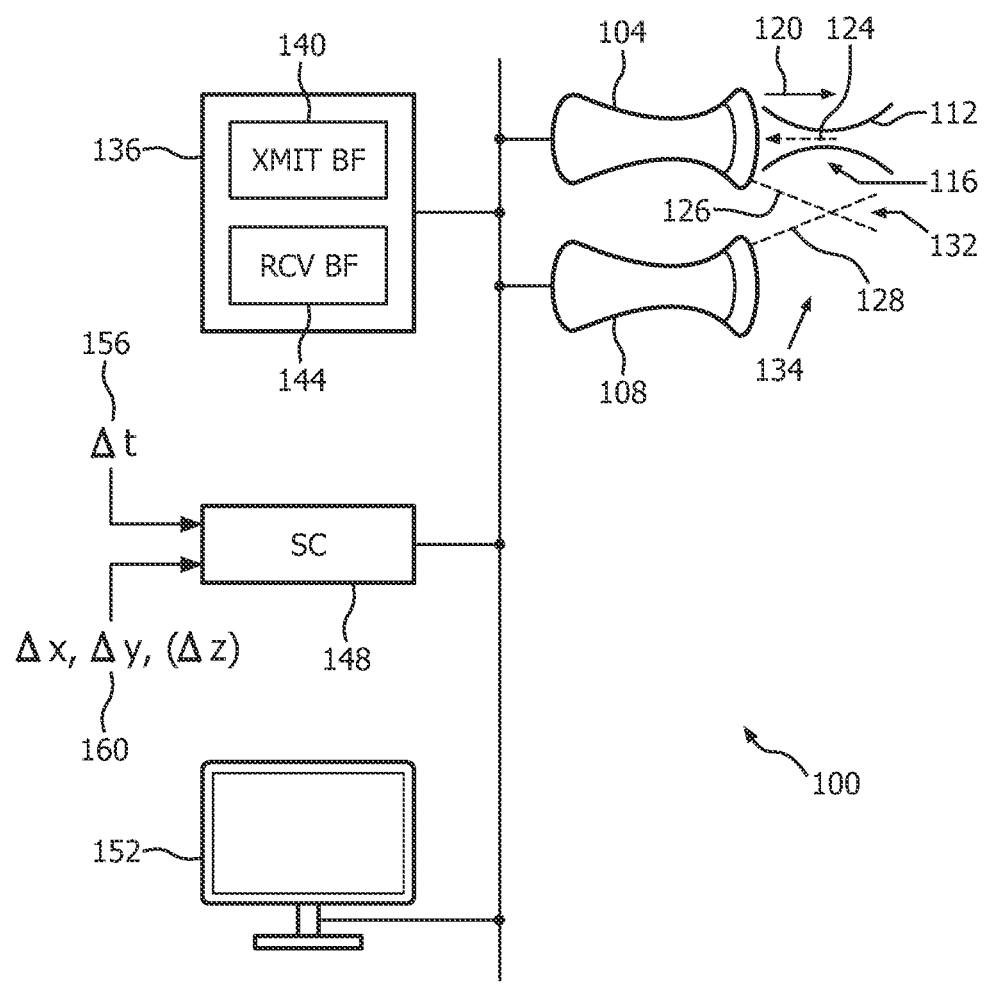
FIG. 1 is a schematic diagram showing, by example, an imaging device for ultrasound acquisition synchronization technology based on multiple acoustic windows, according to the present invention.

FIG. 1 depicts, by illustrative and non-limitative example, an imaging device 100 operable for ultrasound acquisition through multiple acoustic windows and synchronization of the acquisition. The device 100 includes multiple probes 104, 108.

For one of the probe 104, a transmit beam (or "transmit") 112 with a focus 116 is shown in FIG. 1 for illustrative purposes. The beam 112 travels in the direction 120 indicated. On receive, a responsive receive beam (or "receive" or "A-line") 124 of image samples is progressively acquired via the ultrasound echoes from increasing imaging depths returning in a direction opposite to the transmit direction 120. Since the probe 104 has a phased array, many beams 112 are, via the steering capability, emitted in differently angled directions during the course of a scan. The protocol is a transmit 112, followed by the corresponding receive 124. This is then repeated in an adjacent direction. In particular, the beams 112, 124 rotate clockwise, in a scan, in FIG. 1.

All of the above applies also to the second probe 108.

Some of the imaging of the two probes will accordingly overlap as represented by the crossing of the field-of-view lines 126, 128. In addition, the scanning of the two probes 104, 108 is synchronized. For one thing, start of scanning for the second probe 108 is delayed with respect to start of scanning for the first probe 104. In addition, in an overlap region 132, the scanning of the two probes 104, 108 interleaves beam by beam. The synchronized scanning of the two probes 104, 108 collectively amounts to a composite scan 134.

Although merely two probes 104, 108 are illustrated, any number of additional probes can be laterally added, resulting each time in an additional analogous overlap region 132.

Also, the scanning can be three-dimensional (3D). In such an alternative embodiment, each transmit/receive in a given direction in FIG. 1 actual entails acquisition of an imaging plane perpendicular to the sheet of FIG. 1. The planar acquisition can, in itself, be a scan, orthogonal to the scans that overlap resulting in the overlap region 132. The planar acquisitions would therefore follow one after another, interleavingly with respect to the two probes 104, 108. The 3D reconstruction could therefore be based on a single sweep of the scans that overlap.

The imaging device 100 further includes image acquiring circuitry 136 for operating the probes 104, 108 to acquire imaging. The circuitry 136 includes a transmit beamformer 140 and a receive beamformer 144 for respectively forming transmit beams 112 and receive beams 124.

Also included in the imaging device 100 is scan conversion circuitry 148 and a display 152. The scan conversion circuitry 148, in addition to weighting image samples spatially, or based on geometry, weights the same samples temporally. Thus, an input to the scan conversion is elapsed time 156, as well as spatial distance 160. The spatial distance is denoted by Δx, Δy for 2D scanning and Δx, Δy, Δz for 3D scanning. In particular, although 2D pixel reconstruction may use a circle of proximity for choosing samples, the 3D analog is a sphere of proximity.

The elapsed time 156 is an indicator of the recency of a sample. At the time temporal weights are applied, a smaller elapsed time 156 means that the sample is less "out-of-date." The sample is to accordingly be given, in a weighted average computation, extra temporal weight in comparison to a less recent sample. The temporal weights are based on, e.g., proportional to, relative recency. They can be made inversely proportional to elapsed time 156. Alternatively, a difference in elapsed time 156 may be used as a measure of relative temporal weights. More details on these computations and examples are presented further herein below.

Figure 2:
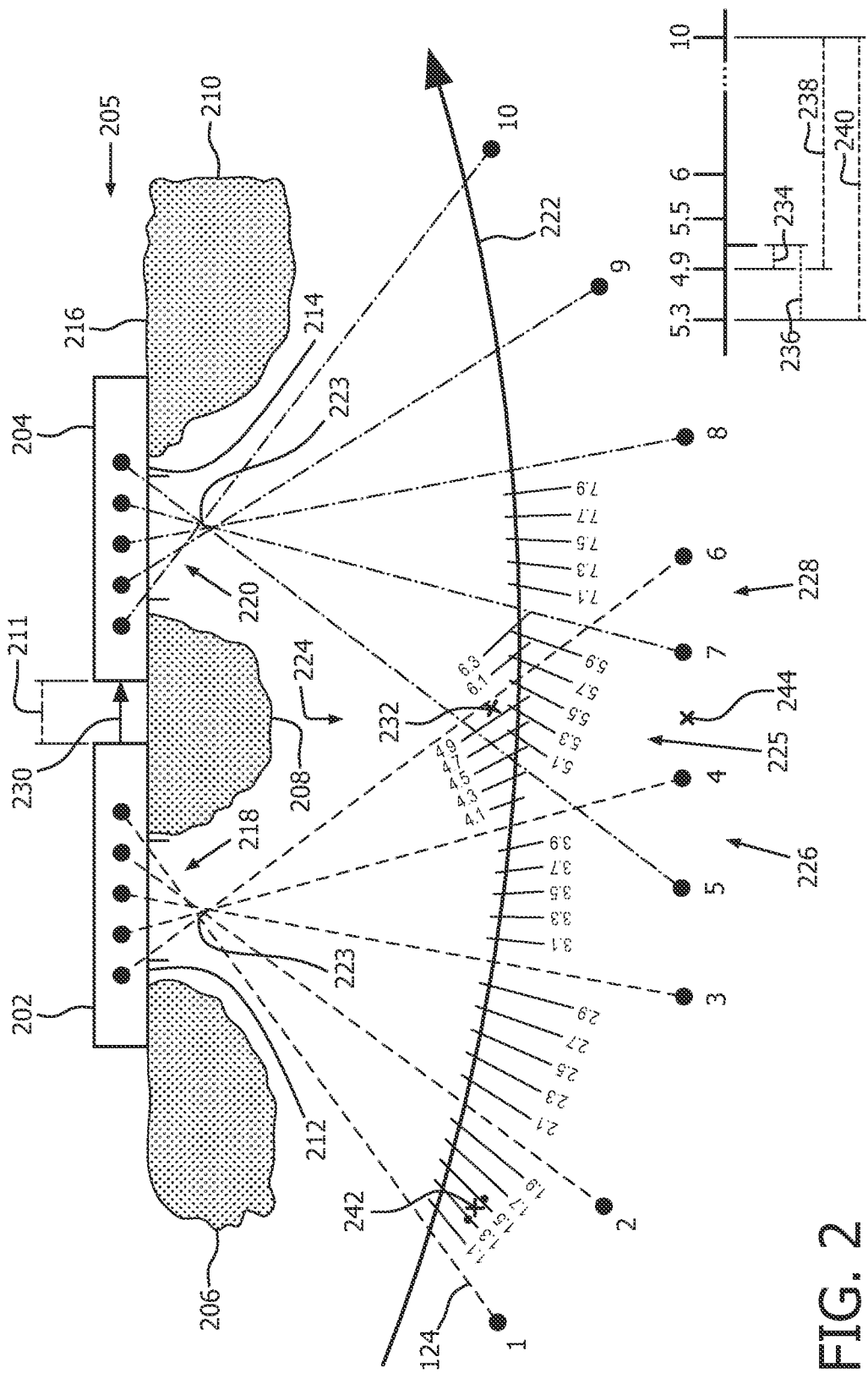
FIG. 2 is a conceptual diagram exemplifying scanning and both spatial and temporal weighting in scan conversion using the device of FIG. 1.

FIG. 2 provides an example of scanning and of the subsequent scan conversion. Two phased array transducers 202, 204 of the respective probes 104, 108 are, while held in place side-by-side 205, used to jointly image an area of the chest of a patient. An occlusion layer is composed of ribs 206, 208, 210 of the patient. The probes 104, 108 are disposed spaced apart 211 to image around the center rib 208. The transducers 202, 204 have respective ultrasound-interface surfaces 212, 214. The surfaces 212, 214 are pressed into contact with the skin 216 of the patient, although there is a thin intervening layer of acoustic gel. Receive beams shown by the dashed and dot-dashed lines pass through the skin 216, as do the respective transmits. The portions of the skin 216 through which the imaging is done are referred to herein after as acoustic windows. Illustratively in FIG. 2, short vertical line pairs for each transducer 202, 204, delimit respective acoustic windows 218, 220. In the current embodiment, the focus 116 of each transmit is on an analytical construction referred to herein as a synchronization, or "synch", line 222. More generally, however, the synchronization line 222 may be any line that the receive beams 124 of the composite scan traverse in order, left to right. The shape of the line 222 is not limited. In FIG. 2, the shape is defined by the focuses, or "depths of focus", 116. It is also configured in FIG. 2 such that the respective bisectors of the fields of view of the acoustic windows 218, 220 intersect so as to delimit radii of curvature for the synch line 222.

For the first probe 104, a first receive 124 is marked "1" in FIG. 2. Four subsequent receives are marked "2", "3", "4" and "6", respectively.

For the second probe 108, five receives 124 are marked "5", "7", "8", "9" and "10", respectively.

Each probe 104, 108, does a rotational scan, and the two scans are synchronized into a composite scan. A center of rotation 223 of the rotational scan is disposed in front of the ultrasound-interface surface 212, 214. In a 3D scanning context, it is a line of rotation.

The 10 markings relate to a firing sequence of the transmits 112 or, equivalently, an ordering of the receives 124.

The 10 beams 124 mentioned herein above traverse the synch line 222 one after another in a lateral direction (left-to-right). The progression in that direction seen in FIG. 2 as strictly increasingly in that direction. More generally, it monotonically progresses in that direction.

In actual sampling, there would be many more than 10 beams. Typically, there would be more than 100 beams.

Additional intermediate beams 124 are shown in FIG. 2. In between beams "1" and "2", for example, there are beams 1.1, 1.3, 1.5, 1.7 and 1.9. Also, with respect to the first probe 104 and by way of further example, there are two beams 6.1 and 6.3 between beams "6" and "7".

All of the beams in FIG. 2 traverse the synch line 222 one after another in a lateral direction (left-to-right).

For instance, starting with beam 3.9, the order in which the beams 124 traverse the synch line 222 is: 4, 4.1, 4.3, 4.5, 5, 5.1, 4.7, 5.3, 4.9, 5.5, 6, 6.1, 5.7, 6.3, 5.9, etc. This order is equivalently the firing order of the respective transmits 112.

In a central region 224 where the scanning of the two probes 104, 108 spatially overlaps, the scanning of the two probes temporally interleaves with respect to a portion 225 of the synch line 222 that laterally extends across the central region. This is seen from a subset of the above scanning order sequence: 4.5, 5, 5.1, 4.7, 5.3, 4.9, 5.5, 6, 6.1, 5.7, 6.3, 5.9. Illustratively, when the two probes 104,108 are listed correspondingly for the beams, the subset sequence is: 4.5 (probe 1), 5 (probe 2), 5.1 (probe 2), 4.7 (probe 1), 5.3 (probe 2), 4.9 (probe 1), 5.5 (probe 2), 6 (probe 1), 6.1 (probe 1), 5.7 (probe 2), 6.3 (probe 1), 5.9 (probe 2). The scanning sequence can instead be arranged such that the interleaving is a toggling, i.e., binary, alternation between the two probes 104, 108. The ultrasound-interface surfaces 212, 214 face opposite sides 226, 228 of the central region 224. The composite scan is in a lateral direction 230 between the two acoustic windows 218, 220.

To reconstruct a spatially intermediate pixel 232, at least two neighboring samples are selected. One technique would be to select samples that distance-wise are within a proximity threshold $T_P$. In FIG. 2, four samples are chosen from four respective receive beams 5.3, 4.9, 5.5, and 6. The threshold $T_P$ may be iteratively applied, reducing it each time, in order to reduce the number of samples used in reconstructing the pixel 232.

The sample from receive beam 4.9 is spatially weighted more heavily in the reconstruction, i.e., scan conversion, than is the sample from receive beam 5.3, as evidenced from the respective distances 234, 236, from the pixel 232, shown in FIG. 2. In particular, the first distance 234 is shorter than the second distance 236.

Temporally, it is assumed here, for purposes of illustration, that scan conversion is executed at the conclusion of the composite scan; although, the scan conversion could occur more frequently for greater frame rate.

At the time of scan conversion for the pixel 232, the elapsed times 156 with respect to the samples used for the scan conversion are indicative of the relative relevance of those samples in the scan conversion.

In particular, the elapsed time 238 for the beam 4.9 sample is less than the elapsed time 240 for the beam 5.3 sample. So, temporally too the beam 4.9 sample is weighted more heavily than is the beam 5.3 sample.

However, the relative spatial and temporal weightings could just as easily turn out to be much different for any given pixel.

Firstly and by way of example, a pixel 242 may be closer to receive beam 1.3 than to receive beam 1.5, and therefore more heavily spatially weighted by the former beam, and yet temporally accord, for its reconstruction, more weight to the latter beam since the latter beam is, at the time of weight application (i.e., reconstruction or scan conversion, for the pixel 242), more recent.

Secondly, further away from the synch line 222, temporal weighting can assume more significance. Thus, for example, the temporal weighting for pixel 244 accounts for the difference between the elapsed time for beam 4.5 and beam 5.5. The synch line 222 shows that this is a relatively large time difference. In the shallower than synch line 222 context, a pixel right near the intersection of receive beams 4 and 5 also is computed based on a relatively large time difference, as seen from where the two beams intersect the synch line. In fact, samples on the synch line 222 that are or happen to be chosen for reconstructing a pixel can, alternatively, be equally weighted temporally or be just weighted spatially.

In standard scanning, the time differential between the scanning of the two acoustic windows causes motion artefacts in the central region.

However, according to the techniques proposed herein, synchronizing beam-wise the scanning from respective, laterally-aligned acoustic windows in combination with temporal weighting in scan conversion mitigates centrally-located motion artefacts. The resulting depiction on the display 152 of live moving images is relatively artefact-free and biased in favor of more recently acquired image data for greater fidelity.

Figure 3A:
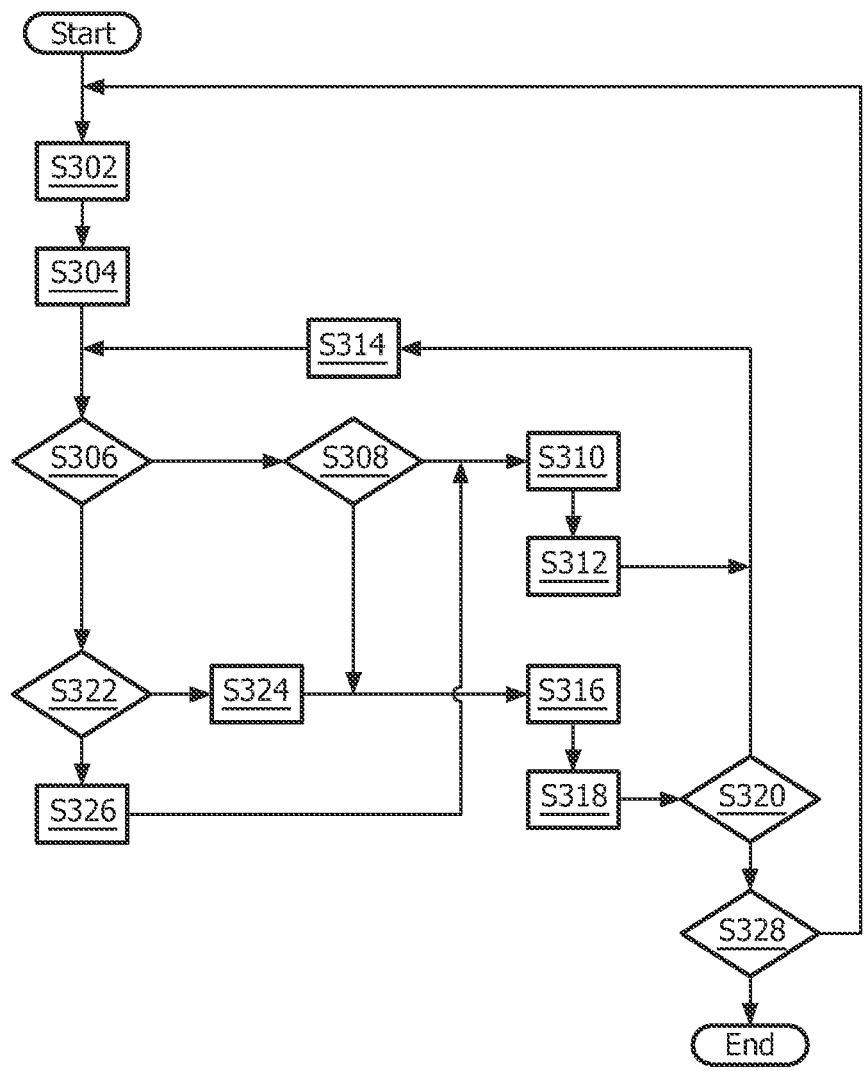
FIGS. 3A-3C are flow charts exemplary of scanning and pixel reconstruction, according to the present invention.

The composite scan shown in FIG. 2 progresses, with respect to sampling on the synch line 222, strictly increasingly in the same lateral direction 230 between the two acoustic windows 218, 220. The temporal interleaving of the acoustic windows 218, 220 with respect to receive beamforming can, as mentioned herein above, be a toggling alternation between the two windows. This is demonstrated in FIG. 3A, for the case of a 2D composite scan. The scanning of the first probe 104 is initialized to start from the left (step S302). A probe alternation flag is cleared (step S304). If there is currently no spatial overlap of the scanning of the two probes 104, 108 (step S306), query is made as to whether this is currently the first temporal half of the scan (step S308). If it is the first half (step S308), the first probe 104 transmits a beam 112 (step S310) and receives the return beam 124 (step S312). Beam steering is shifted rightward with respect to the synch line 222 (step S314), and return is made to step S306. If, instead, this is currently the second temporal half of the scan (step S308), the second probe 108 transmits a beam 112 (step S316) and receives the return beam 124 (step S318). If another beam remains for the current scan (step S320), beam steering is shifted rightward with respect to the synch line 222 (step S314), and return is made to step S306. If, on the other hand, there currently is spatial overlap of the scanning of the two probes 104, 108 (step S306), query is made as to whether the probe alternation flag is clear (step S322). If the flag is clear (step S322), the flag is now set (step S324) and processing branches to step S316. Otherwise, if the flag is instead not clear (step S322), the flag is now cleared (step S326), and processing branches to step S310. When the point is reached in the scan that there is no further beam 124 (step S320), query is made as to whether a next scan is to be made (step S328). If a next scan is to be made (step S328), processing returns to the start of the routine, i.e., step S302. Otherwise, if there is no next scan to be made (step S328), the scanning is now complete.

Figures 3B, 3C:
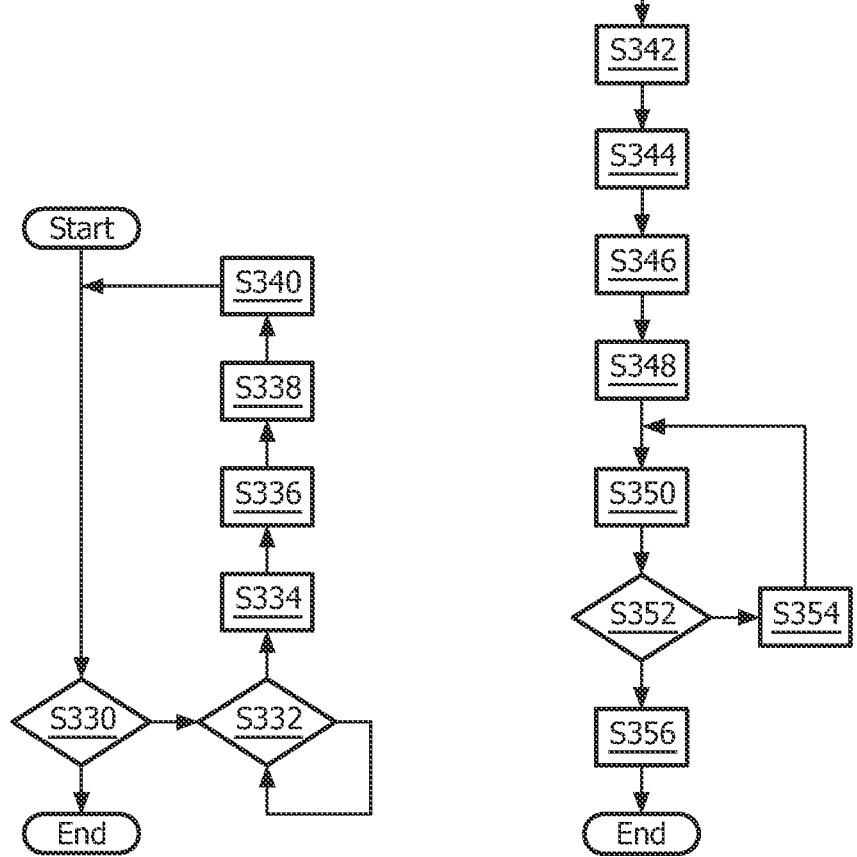

FIGS. 3B and 3C describe temporal weighting as a consideration additional to spatial weighting in scan conversion.

Referring to FIG. 3B, a time is to be associated with each sample for temporal weighting purposes in pixel reconstruction. For either acoustic window 218, 220 on receive, while the receive window has not yet expired (step S330), and when a sample is received (step S332), a time stamp of acquisition is linked with the sample (step S334). A duration of return flight is determined (step S336). In particular, ultrasound travels through soft body tissue at the speed of 1540 meters per second. There exists a known distance between the field point at which the sample is taken and a transducer element by which a return echo from the field point is sensed. Any element in the receive aperture at any time during the receive window, or any combination of such elements, may be considered. Also, the time of the transmit, and its directionality to the field point, are known. Therefore, the difference between the time of the time stamp and the time of the transmit can be divided into a transmit time to the sample and an echo return time. The duration of return flight is subtracted from the time stamp of acquisition to yield a time stamp of ultrasound reflection in acquiring the sample (step S338). The reflection time stamp is recorded in a spatial matrix, in the entry corresponding to the field point (step S340). Alternatively, for simplicity, the matrix can be filled with either the time of the transmit, especially if only one sample per proximal receive line 126 is to be chosen for pixel reconstruction, or the time of sample acquisition at the transducer. In any event, the time stamp constituting the matrix entry is specifically associated with the sample at the respective field point.

Pixel reconstruction is exemplified in FIG. 3C. The current time is recorded (step S342). A current pixel 232 to be reconstructed is selected (step S344). Samples within a predetermined proximity $T_P$ of the pixel 232 are chosen (step S346). One or more samples from each receive beam 124 may qualify for being chosen. Processing points to the first of the chosen samples (step S348). The matrix entry for the current sample, i.e., for its field point position, is subtracted from the current time that was recorded in step S342 (step S350). The subtraction yields the elapsed time 156. If there exist more chosen samples for the current pixel to be reconstructed (step S352), processing points to the next sample (step S354), which serves as the current sample upon branching back to the subtraction step S350. Otherwise, if there are no remaining chosen samples (step S352), the current pixel 232 is weighted both spatially and temporally (step S356). The spatial weights $w_{s1}, w_{s2}, \ldots, w_{sn}$ are each within the range [0,1] and collectively add up to unity. Likewise, the temporal weights $w_{t1}, w_{t2}, \ldots w_{tm}$ are each within the range [0,1] and collectively add up to unity. There are at least two spatial weights and at least two temporal weights. They may be averaged to produce an overall weight $w_{oi}=(w_{si}+w_{ti})/2$, $i=1, \ldots, n$. The overall weights are then applied to the samples as in any scan conversion for reconstructing respective intermediate pixels. In the simplest case of two chosen samples, with the pixel midway in between, the weights are applied to the respective sample brightness values to reconstruct the pixel with a brightness that is the weighted average resulting from the applied weights.

In some embodiments, ultrasound receive beamforming yields beamformed samples, based upon which spatially intermediate pixels are dynamically reconstructed. The samples have been correspondingly derived from acquisition through respectively different acoustic windows. The reconstructing is further based on temporal weighting of the samples. In some embodiments, the sampling is via synchronized ultrasound phased-array data acquisition from a pair of side-by-side, spaced apart acoustic windows respectively facing opposite sides of a central region to be imaged. In particular, the pair is used interleavingly to dynamically scan jointly in a single lateral direction in imaging the region. The acquisition in the scan is, along a synchronization line extending laterally across the region, monotonically progressive in that direction. Rotational scans respectively from the window pair are synchronizable into a composite scan of a moving object. The line can be defined by the focuses of the transmits. The progression may strictly increase.

Clinical applications of the proposed technology include imaging the heart, kidneys, liver and include the imaging other obstetrics/gynecological and neonatal procedures.

Although methodology of the present invention can advantageously be applied in providing medical diagnosis for a human or animal subject, the scope of the present invention is not so limited. More broadly, techniques disclosed herein are directed to improved wide-view imaging of moving structures, in vivo or ex vivo.

While the invention has been illustrated and described in detail in the drawings and foregoing description, such illustration and description are to be considered illustrative or exemplary and not restrictive; the invention is not limited to the disclosed embodiments.

For example, an array of laterally-adjacent acoustic windows may be two-dimensional, in which case pair-wise adjacent, even slant-wise adjacent, windows may follow the above-described scanning protocol.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:
1. An ultrasound imaging device comprising:
an image acquiring circuitry including a receive beamformer for beamforming to yield beamformed samples, wherein the image acquiring circuitry is coupled to a pair of imaging probes and configured to operate the pair of imaging probes for an acquisition through a pair of acoustic windows, wherein the beamformed samples are associated with corresponding spatial locations, and wherein the acquisition is performed in a scan and wherein the acquisition via the pair of acoustic windows alternates between the two acoustic windows in a central region of the scan, wherein the acquisition progresses in a same direction along a synchronization line, wherein the synchronization line includes a portion residing within the central region and extends laterally across the central region, wherein the acquisition via the pair of acoustic windows is performed along the portion residing within the central region, and during joint and interleaving scan between the pair of imaging probes, and wherein the synchronization line is traversed by the beamformed samples; and
a scan conversion circuitry configured to, based on the beamformed samples, dynamically reconstruct spatially intermediate pixels corresponding to spatial locations different than the spatial locations of the beamformed samples, based at least in part on a temporal weighting of the beamformed samples, wherein the beamformed samples are correspondingly derived from the acquisition through respectively different acoustic windows, including the pair of acoustic windows, wherein the temporal weighting is inversely proportional to a relative recency of the beamformed samples.

2. The device of claim 1, wherein a probe of the pair of imaging probes comprises a phased array for beamforming.

3. The device of claim 1, wherein the scan is in direction that is between the pair of the acoustic windows acquiring data in the scan.

4. The device of claim 1, further comprising a three-dimensional reconstruction which is performed based on a single performance of the scan.

5. The device of claim 1, wherein the scan conversion circuitry is configured to reconstruct with the pair of the acoustic windows being disposed side by side and spaced apart.

6. The device of claim 1, wherein the scan conversion circuitry is configured to reconstruct with an overlap region of imaging, based on the acquisition, wherein the overlap region is disposed centrally with respect to the pair of acoustic windows.

7. The device of claim 1, wherein the pair of the acoustic windows respectively face opposite skies of the central region.

8. The device of claim 1, wherein the image acquiring circuitry is further configured to issue beams in different directions having respective focuses, wherein the focuses are disposed along the synchronization line.

9. The device of claim 1, wherein the pair of the acoustic windows are arranged laterally, wherein the device configured to acquire through the pair of the acoustic windows via respective, synchronized rotational scans in a same lateral direction in which the pair of the acoustic windows is arranged.

10. The device of claim 1, wherein the scan conversion circuitry is further configured for temporally weighting respective ones of the beamformed samples when reconstructing a pixel from among the spatially intermediate pixels, and wherein the temporal weighting is based on time stamps associated specifically with the respective beamformed samples.

11. The device of claim 1, wherein the acquisition is performed via respective rotational scans.

12. The device of claim 11, wherein the acquisition from a rotational scan from among the respective rotational scans is via a transducer having an ultrasound-interface surface, a center of rotation for the rotational scan being disposed in front of the ultrasound-interface surface.

13. A method for synchronized ultrasound phased-array data acquisition from a pair of side-by-side, spaced apart acoustic windows of a pair of imaging probes respectively facing opposite sides of a central region to be imaged, comprising:
using the pair of acoustic windows of the pair of imaging probes interleavingly to dynamically scan jointly in a single lateral direction in imaging the central region, wherein the data acquisition in the dynamically scan being along a synchronization line, wherein the synchronization line includes a portion residing within the central region and extending laterally across the central region, wherein the data acquisition via the air of acoustic windows alternates between the two acoustic windows in the central region, and wherein the dynamically scan is monotonically progressive in the single lateral direction, and the single lateral direction is a direction between the pair of acoustic windows;

beamforming to yield beamformed samples, wherein the beamformed samples are associated with corresponding spatial locations, and wherein the synchronization line is traversed by the beamformed samples; and dynamically reconstructing, based on the beamformed samples, spatially intermediate pixels corresponding to spatial locations different than the spatial locations of the beamformed samples, wherein the beamformed samples are correspondingly derived from the data acquisition through respective different acoustic windows, and wherein the dynamically reconstructing is further based on a temporal weighting of the beamformed samples, wherein the temporal weighting is inversely proportional to a relative recency of the beamformed samples.

14. A non-transitory computer readable medium embodying a program for scan conversion based on beamformed samples, the program having instructions executable by a processor for performing a plurality of acts, among the plurality of acts there being the acts of:

deriving the beamformed samples from acquisition through respectively different acoustic windows of a pair imaging probes, wherein the beamformed samples are associated with corresponding spatial locations, and wherein the acquisition is performed in a scan and the acquisition via the different acoustic windows alternates between the different acoustic windows in a central region of the scan, wherein the acquisition progresses in a same direction along a synchronization line, wherein the synchronization line includes a portion residing within the central region and extends laterally across the central region, wherein the acquisition via the different acoustic windows is performed along the portion residing within the central region, and during joint and interleaving scan between the pair of imaging probes, and wherein the synchronization line is traversed by the beamformed samples; and dynamically reconstructing spatially intermediate, pixels corresponding to spatial locations different than the spatial locations of the beamformed samples based, in part, on temporal weighting of the beamformed samples, and wherein the temporal weighting is inversely proportional to a relative recency of the beamformed samples.

* * * * *